United States Patent
Visweswara et al.

(10) Patent No.: US 12,070,302 B2
(45) Date of Patent: Aug. 27, 2024

(54) ON-BODY SENSOR SYSTEM AND METHOD

(71) Applicant: KONINKLIJKE PHILIPS N.V., Eindhoven (NL)

(72) Inventors: Ashoka Sathanur Visweswara, Amstelveen (NL); Mark Thomas Johnson, Arendonk (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 827 days.

(21) Appl. No.: 17/254,895

(22) PCT Filed: Jun. 26, 2019

(86) PCT No.: PCT/EP2019/067064
§ 371 (c)(1),
(2) Date: Dec. 22, 2020

(87) PCT Pub. No.: WO2020/002461
PCT Pub. Date: Jan. 2, 2020

(65) Prior Publication Data
US 2021/0212590 A1 Jul. 15, 2021

Related U.S. Application Data

(60) Provisional application No. 62/691,203, filed on Jun. 28, 2018.

(51) Int. Cl.
*A61B 5/06* (2006.01)
*A61B 5/00* (2006.01)
(52) U.S. Cl.
CPC ............ *A61B 5/062* (2013.01); *A61B 5/0028* (2013.01); *A61B 5/6824* (2013.01);
(Continued)

(58) Field of Classification Search
CPC .......... A61B 2560/0271; A61B 5/0028; A61B 5/062; A61B 5/6824; A61B 5/6833; A61B 5/684
See application file for complete search history.

(56) References Cited

U.S. PATENT DOCUMENTS

| | | | |
|---|---|---|---|
| 9,241,673 B2 * | 1/2016 | Sabesan | ............... A61B 5/0245 |
| 2015/0094605 A1 | 4/2015 | Sabesan et al. | |
| 2017/0086023 A1 | 3/2017 | Tartz et al. | |

FOREIGN PATENT DOCUMENTS

WO 2017167887 A1 10/2017

OTHER PUBLICATIONS

International Search Report and Written Opinion, International Application No. PCT/EP2019/067064, Mailed on Sep. 11, 2019.
(Continued)

*Primary Examiner* — Amanda K Hulbert

(57) ABSTRACT

An on-body sensor system (30) comprises means for determining a position of a skin interface unit (34) based on transmission and receipt of electrical signals to the unit from a known transmitter (32) location, transmitted via electrical channels of the body. By comparing sensed signal characteristics of the received signals with a plurality of sets of pre-determined signal characteristics, each set associated with one of a plurality of different reference positions and/or orientations of the receiver (34) on the body, it is possible to derive an indication of the position of the receiver unit on the body.

17 Claims, 8 Drawing Sheets

(52) U.S. Cl.
CPC ............ *A61B 5/6833* (2013.01); *A61B 5/684* (2013.01); *A61B 2560/0271* (2013.01)

(56) References Cited

OTHER PUBLICATIONS

Cho, N. et al., "The Human Body Characteristics as a Signal Transmission Medium for Intrabody Communication", IEEE Transactions on Microwave Theory and Techniques, vol. 55, No. 5, May 2007.
Zhang, Y. et al., "SkinTrack: Using the Body as an Electrical Waveguide for Continuous Finger Tracking on the Skin", Carnegie Mellon University, 2016.
Belay, A. et al., "Indoor Localization at 5GHz Using Dynamic Machine Learning Approach (DMLA)", Proceedings of the 2017 IEEE International Conference on Applied System Innovation IEEE-ICASI 2017—Meen, Prior & Lam (Eds).
Dash(2015). Dash, Shubhra Shubhankari, et al. "A Survey on localization in Wireless Sensor Network by Angle of Arrival." International Journal 2: 115-122.
Grant S. Anderson, C. G. (2013). Body Coupled Communication: The Channel and Implantable Sensors. IEEE Body Sensor Networks.
Joonsung Bae, e. (2012). The Signal Transmission Mechanism on the Surface of Human Body for Body Channel Communication. IEEE Transactions on Microwave Theory and Techniques.
Maicon D. Pereira, e. (2015). Characterization and Modelling of the Capacitive HBC Channel. IEEE Transactions on Instrumentation and Measurement.
Sangkil, e. (2014). Ambient RF Energy Harvesting Technologies for Self-Sustainable Standalone Wireless Sensors Platforms. IEEE Micro.
Technologies, D. (2015). RF Energy Harvesting for the Low Energy Internet of Things.

* cited by examiner

ON-BODY SENSOR SYSTEM AND METHOD

This application is the U.S. National Phase application under 35 U.S.C. § 371 of International Application No. PCT/EP2019/067064, filed on 26 Jun. 2019, which claims the benefit of U.S. Provisional Application No. 62/691,203, filed 28 Jun. 2018. These applications are hereby incorporated by reference herein.

FIELD OF THE INVENTION

The various embodiments described herein relate to an on-body or handheld sensor system having one or more on-body or handheld sensor elements, and method for configuring the same.

BACKGROUND OF THE INVENTION

On-body sensing systems permit accurate long-term monitoring of physiological parameters of a subject. On-body systems are based on use of wearable devices or units, including for instance patches, which are attached to or mountable on the body and maintain a relatively stable position over time. As another example, handheld devices are positioned according to the body and may require a relatively stable position over time. By electrically interfacing with the skin or body, vital signs or other parameters may be monitored.

On-body systems may typically be used in low acuity settings such as a general ward and also at a subject's home. Improved reliability in physiological parameter monitoring in general wards is needed to reduce mortality rates, by enabling detection of any deterioration in condition as early as possible. The capacity to monitor reliably at a subject's home also permits earlier discharge of patients without risk of undetected deterioration. Monitoring will typically continue up to 30 days from discharge for example.

In the case of patches, in many cases these need to be changed every 2-3 days because of depleted battery charge, degradation of adhesion and/or skin irritation. As a result, it falls to a patient him- or herself and/or an informal care giver such as a relative to replace and re-attach the patch. In some cases, the patch has to be moved to other alternative locations and orientations. Accurate placement of the patch upon replacement is important to ensure that physiological parameters are correctly determined.

Similarly, accurate placement is imperative for handheld devices that are in contact with the body such as handheld imaging sensors and/or devices. For example, accurate placement of a handheld ultrasound device that may include capacitive micromachined ultrasonic tranducer (cMUT) arrays for image acquisition is essential for the registration of the correct physiological images. Accordingly, systems, methods, and/or devices to ensure proper placement (orientation and positioning) of any sensor-related device is desirable.

Academic work has previously described an electrical field model of the human body. The model may be used to determine the frequency response of the human body as a signal transmission medium. It is measured by generating and capacitively coupling an electrical signal having a known frequency and amplitude at one point on the human body. The coupled signal may be sensed and measured at a different, remote point on the body by a sensor. The received signal may be analyzed and various signal properties derived. This process may be repeated for multiple different signals having different transmitter frequencies and also for various distances and body locations of the on-body sensing element relative to the transmitting location.

One example model is presented in Namjum Cho, et al. (2007). The Human Body Characteristics as a Signal Transmission Medium for Intrabody Communication. *IEEE Transactions on Microwave Theory and Techniques*. In this paper, the authors propose a near-field coupling model of the human body based on modelling the human body in terms of three cylinders: two for the arms and one for the human torso. This is illustrated in FIG. 1.

As shown in FIG. 1(*a*), the arms and the human torso are segmented with 10 cm long unit blocks, each with resistances and capacitances. The arms and the torso are together modelled as distributed RC network as shown in FIG. 1(*b*). In a similar manner, a human leg may be modelled with corresponding resistances and impedances. The arm model has resistance and capacitance with subscript "A" and the torso has resistance and capacitance with subscript "T".

One practical implementation of the signal transmission and sensing approach is presented in Zhang, Y. et al, 2016, May. "Skintrack: Using the body as an electrical waveguide for continuous finger tracking on the skin". In Proceedings of the 2016 CHI Conference on Human Factors in Computing Systems (pp. 1491-1503).

This paper proposes a continuous finger tracking technology called SkinTrack. SkinTrack is a wearable system that enables continuous touch tracking across the skin. The system comprises a ring, which emits a continuous high-frequency AC signal, and a sensing wristband embodying multiple sensor electrodes. Due to the phase delay inherent in propagating the high frequency AC signal through the body, a phase difference may be observed between pairs of electrodes. The SkinTrack system measures these phase differences to compute a 2D coordinate location of the subject's finger touching on their skin. The resolution (i.e. accuracy) of SkinTrack method is approximately 7 mm.

The same paper describes a method whereby the phase angle difference between the sensed signals at two different locations on the human body is used as a measure of localization of the signal transmitter with respect to the sensors. FIG. 2 schematically illustrates the technique, where the transmitter is in the form of a ring 12. The location of the transmitter relative to two sensor electrodes 14*a*, 14*b* on a smartwatch is identified using the technique.

When an 80 MHz RF signal is used, the wavelength of the electromagnetic wave propagating through the human body is around 91 cm. This results in phase angle difference of approximately 4°/cm for one single cycle of the wave. If the localization is performed within one wavelength of the RF signal (i.e. within around 91 cm), then it is possible to derive an indication of the position of the transmitter with relative to the two sensors by measuring the phase angle difference between the two received signals.

When monitoring physiological parameters, accurate placement of patches is critical for correct functioning. And when using various other sensing devices, such as the handheld imaging sensor devices described herein, placement of the device is essential for correct results. However, in the home-based monitoring and/or other regimes described above, the patient, a non-clinician caregiver, and/or a medical professional is required to place the patches him- or herself. This may be challenging, even with medical training, and especially without medical training, and even more so for patients having e.g. poor eyesight, dexterity, or having reduced cognitive function. A solution to facilitate reliable placement of a patch and/or other sensing device as described herein at a correct location would therefore be of value, to increase reliability of monitoring, sensing, and/or imaging.

SUMMARY OF THE INVENTION

Known approaches and models to assist in placement of sensor elements remain very restrictive in terms of the degree to which they permit a position of a transmitter to be uniquely identified. Crucially, while it has been shown how to derive an indication of a relative distance between a transmitter and receiver, this does not allow a position of either element on the body to be uniquely identified. Hence, accurate position determination is not yet possible. This makes known approaches unsuitable for cases where precise and unique localization of an element on the body is required. Furthermore, even the known approach for determining a relative distance is only achievable where the transmitter and receiver are kept within a limited separation range of one wavelength (one cycle), which is very restrictive.

According to examples in accordance with an aspect of the embodiments described herein, there is provided an on-body or handheld sensor system, comprising:

at least two skin interface units for coupling electrical signals into and/or out of the body of a subject, including at least one transmitter unit for placement against a known region of the skin of the subject for coupling signals into the body, and at least one receiver unit for placement at a remote location, for sensing the coupled signals;

a controller operably coupled with the skin interface units and adapted to control transmission of signals between the at least one transmitter unit and receiver unit, and to derive a set of signal characteristics associated with each signal received at the receiver, the characteristics being dependent on position and/or orientation of the receiver unit;

the controller having access to a dataset comprising a plurality of pre-determined sets of signal characteristics, each set associated with one of a plurality of different reference positions and/or orientations of the receiver on the body;

wherein the controller is configured to derive an indication of position and orientation of the at least one receiver based on comparing the derived set of signal characteristics for the received signals with the pre-determined sets of signal characteristics, and generate output information based on the derived indication of position and orientation.

The embodiments described herein make use of at least two skin coupling elements, at least one being configured as a signal transmitter, and at least a second being configured for receiving transmitted signals. The embodiments described herein are based on using the receiver to derive a set of multiple different signal characteristics associated with the sensed signal. These may be directly measured from the signal or they may be derived through processing or calculation based on signal measurements. This set of characteristics forms a unique 'body channel fingerprint' for the receiver unit position, which uniquely characterizes the particular position and orientation of the receiver. By providing a predetermined collection of similar sets of signal characteristics for multiple different possible reference positions and orientations (i.e. reference fingerprints), it is possible to derive by comparison an indication of the current unique position and orientation of the receiver.

Hence the basic approach of body channel sensing discussed in the prior art has been developed by the inventors, to permit unique localization of a receiver element, e.g. a sensor patch, to be realised.

The embodiments described herein make use of a controller. The controller may be a separate (dedicated) controller or the control function may be performed by one or more of the skin interface units themselves. Hence, in the latter case, the controller may be a distributed controller. Hence one or more of the skin interface units may comprise the controller in some examples, i.e. the control function may be distributed among the skin interface units of the system itself. In some examples, each of the skin interface units may comprise a local control module for performing at least part of the control functionality of the overall system. For instance each may control at least its own transmitting or receiving function. One of the units may be designated to perform the processing or determination steps (e.g. determining an indication of position). There may be performed a configuration step in which the skin interface units communicate and designate one of the units as responsible for the determination steps.

In all explanations and descriptions above and below, reference to a controller may be taken as reference to either a dedicated control unit or to one or more of the skin interface units of the system performing the relevant control function.

The electrical signals are electrical stimuli applied to the skin or body. They are carried or transported by the body through electrical body channels. They may be AC signals. The signals may be capacitively coupled into the body, or inductively coupled into the body. The same or a different coupling mechanism may be used to couple signals out of the body for sensing.

The system comprises skin interface units for electrically coupling signals into and back from the skin or body. Each may comprise one or more electrodes for electrically interacting or coupling with the skin. Each unit may be preferably for mounting or applying against the skin, either in contact with the skin or in close proximity to it, possibly separated by a small clearance or space.

One or both skin interface units may comprise or consist of a pad, e.g. a patch, for mounting against the skin. Skin interface unit(s) may also include a handheld device, such as a handheld imaging device as described herein.

Optionally, the controller may generate signals and the transmitter unit controlled to apply these signals to the body. Alternatively, the transmitter unit itself comprises means (e.g. circuitry) to generate the signals.

Signals are sensed at a location remote (i.e. separated) from the first skin interface unit. This means a remote location on the body or skin. Preferably the signals generated for coupling into the body are in the RF frequency range 10 MHz to 150 MHz since in this frequency range the body acts as a waveguide for signal transmission.

One or both of the skin interface units may comprise a plurality of skin interfacing electrodes, e.g. skin contacting electrodes.

The system has at least two skin interface units, at least one for generating and transmitting signals (transmitter), and another for sensing the signals at a remote location (receiver). The first and second interface units may be functionally interchangeable, i.e. either may be selectively configured to act as either signal transmitter or signal receiver. The two may be structurally the same in some examples.

The position of the receiver unit may refer to a positioning on the body, or on the skin. Position may mean an absolute position, i.e. a location on body, or may mean a relative position, i.e. relative to the transmitter, e.g. a distance or separation from the transmitter. Orientation may mean an orientation relative to the skin or an absolute orientation (e.g. measured using a gravity sensor and/or compass).

The derived indication of position may be a direct or indirect indication of position. It may be quantitative co-ordinate position for instance. Alternatively, it may be in terms of the reference positions, e.g. it may be an indication of a reference position to which the current position corresponds, or to which it is close.

The dataset may be stored locally, e.g. in a memory comprised by the system, e.g. by the controller. Alternatively, the dataset may be stored remotely, e.g. in the cloud, or on a remote computer with which the controller is communicable.

In advantageous embodiments, the controller may be configured to compare the derived indication of position and orientation with a defined target position and orientation, and to generate guidance information based on said comparison, for guiding a user in positioning the receiver unit at the target position and orientation. The guidance information may form the output information or the output information may include the guidance information for example.

This may be based on comparing the derived signal characteristics with signal characteristics associated with the target position and orientation. The target position and orientation may be pre-programmed in the controller, or may be configurable, e.g. based on user input. The target position and orientation may be one of the plurality of reference positions and orientations in the dataset. In this way, the pre-determined signal characteristics associated with the target position may be accessed from the dataset, which may in examples be used for the comparison.

Guidance toward the target position and toward the target orientation may be performed or indicated in separate steps or stages, for instance starting with position, and then moving to orientation once the position has been correctly attained.

The controller may be adapted to derive an indication of distance between the derived position and the target position based on said comparison, the output information being based on this derived distance. Distance may be a true distance, i.e. in SI units of meters, or may be a locally defined distance in locally defined or relative units. Deriving a distance allows guidance information to be generated indicating how far the receiver needs to be moved to arrive at the target position.

The controller may further be adapted to determine whether the derived distance is within a defined acceptable proximity threshold of the target distance, and to generate guidance information for positioning the receiver closer to the target position only in the case that the distance is outside of the acceptable threshold.

This improves efficiency by setting a broader allowable range of positions to which the receiver may be moved, thereby avoiding a large number of unnecessarily fine adjustments of positions (which could be difficult for a patient with dexterity or eyesight problems). The proximity threshold may be pre-defined, e.g. pre-programmed, or may be configurable, e.g. by user input.

The controller may be adapted to determine a displacement direction between the derived indication of position and the target position, and wherein the output information comprises an indication of this direction. This helps guide the user in moving the receiver closer to the target position. When optionally combined with derived distance information, this allows a complete translation instruction to generated and provided to the user, indicating both a distance and direction for moving the receiver in order to arrive at the target position.

The controller may hence be adapted, based on the derived distance and direction to the target position, to generate guidance information for moving the receiver unit configured to minimize the distance between the receiver and the target position.

The guidance information in this case includes a distance and direction for moving the receiver unit.

According to advantageous embodiments, the at least one receiver unit comprises at least two pairs of skin-coupling electrodes. The two pairs of electrodes are spatially separated. By providing at least two pairs of electrodes, additional (differential) signal characteristics may be measured, such as a phase angle difference between the two electrode pairs or a difference in the measured signal attenuation and/or time of flight of signals at each electrode pair. Furthermore, a greater number of electrodes pairs provides a greater number of degrees of freedom in the sensed signal characteristics.

In particular, the derived set of signal characteristics preferably may include a separate subset of signal characteristics derived for each of the electrode pairs. Signal transmission time and attenuation will be different for each electrode pair owing to its slightly different location relative to the transmitter. Hence the body signal fingerprint for a given receiver unit may be made more comprehensive by sensing separate subsets of signal characteristics for each of a plurality of electrode pairs.

More than one transmitter unit may be provided in some examples. According to one or more embodiments, the controller may configured to identify a total number of transmitter units, and, in the case that that there is more than one, to control transmission of signals by each transmitter unit in turn, and to derive a separate set of signal characteristics associated with signals received from one.

The transmitter units are hence controlled to generate and transmit signals sequentially, with separate sets of signal characteristics derived for each one in turn. These separate sets may be combined into a compound set of signal characteristics which together form the complete body signal fingerprint corresponding to the receiver location. By using two transmitters, a more comprehensive fingerprint is created, meaning more exact characterization of the unique position and orientation may be achieved. This permits more accurate or precise receiver localization.

According to examples, the at least one receiver unit may be in the form of an on-body sensor patch. The at least one receiver unit may be in the form of a handheld device.

The at least one transmitter unit may in examples be in the form of a wearable device for mounting to a particular part of the body, for example a wrist-mountable wearable device. It may thus be for mounting against a pre-determined region of the skin. This helps ensure that a location of the transmitter on the body is stable and well-known, which improves the reliability of the position determination, which relies upon a consistent and reliable transmitter location.

The transmitter unit may thus be a unit shaped to fit to a particular part of the body, e.g. a wearable unit such a watch, ring, arm or ankle band or ear hook for example.

Alternatively, the at least one transmitter unit may be in the form of an off-body device for temporary placement against the skin of a particular part of the body. This should be a unit configured for placement against a known and consistent skin location. For example, the transmitter unit may be in the form of (or incorporated in) a weight scale which the user stands on.

The system may advantageously be for monitoring one or more physiological parameters of a subject, and wherein the receiver unit may be for use in sensing the one or more physiological parameters.

According to examples, the signal characteristics may include one or more of: signal transmission time (between transmission and receipt), signal attenuation between transmitter and receiver, and phase angle difference between at least two electrodes comprised by the receiver unit. Further possible characteristics may include simply a signal amplitude (in volts).

According to examples the signal characteristics may include one or more differential signal characteristics, meaning a difference in the value of a signal characteristic between two pairs of skin-coupling electrodes comprised by the receiver unit. These differential signal characteristics may include for example at least one of: a phase angle difference, time of flight (signal transmission time) difference, signal attenuation between transmission and receipt (path loss) difference, and signal amplitude difference.

Differential signal characteristics are particularly useful in characterizing the orientation state of the receiver device, since the difference in measured signal characteristics at two spatially separated pairs of electrodes will vary in a consistent manner depending upon orientation. This will be described in greater detail below.

Thus the signal characteristics may be directly measured from the signals, or may be derived based on measured signal properties and other information. For example transmission time (i.e. duration) may be based on an arrival time and time of transmission. Signal attenuation may be based on initial signal strength and sensed signal strength. Signal characteristics may hence be based on signal properties both at transmission and at receipt.

The embodiments described herein may be based on comparing the measured set of signal characteristics with a plurality of pre-determined sets of signal characteristics, each associated with one of a plurality of different reference positions and/or orientations of the receiver on the body. These form a dataset.

A method may be provided for generating and storing these pre-determined reference sets of signal characteristics for use in subsequent configuring of skin interface unit positions.

Thus, examples in accordance with the embodiments described herein may include a method of training an on-body or handheld sensing system for configuring placement of skin interface units of the system, the system comprising at least two skin interface units for coupling electrical signals into and/or out of the body of a subject, including at least one transmitter unit for placement against a known region of the skin of the subject for coupling signals into the body, and at least one receiver unit for placement at a remote location, for sensing the coupled signals, and the method comprising:

sequentially placing the at least one receiver unit in each of a plurality of different reference positions and/or orientations on the body, and for each position and/or orientation controlling transmission of signals between the at least one transmitter unit and receiver unit, and deriving a set of signal characteristics associated with the signals received at the receiver for that position and/or orientation; and storing the plural sets of signal characteristics for the plurality of different reference positions, to thereby derive a dataset of pre-determined signal characteristics, the dataset for use in subsequently deriving indications of position and/or orientation of the receiver unit based on comparing sensed signal characteristics with the stored pre-determined characteristics.

A method may provide configuring placement of skin interface units of an on-body or handheld sensing system, the system comprising at least two skin interface units for coupling electrical signals into and/or out of the body of a subject, including at least one transmitter unit for placement against a known region of the skin of the subject for coupling signals into the body, and at least one receiver unit for placement at a remote location, for sensing the coupled signals, the method comprising:

controlling transmission of signals between the at least one transmitter unit and receiver unit, to derive a set of signal characteristics associated with each signal received at the receiver, the characteristics being dependent on position and/or orientation of the receiver unit;

accessing a dataset comprising a plurality of pre-determined sets of signal characteristics, each set associated with one of a plurality of different reference positions and/or orientations of the receiver on the body;

deriving an indication of position and orientation of the at least one receiver unit based on comparing the derived set of signal characteristics for the received signals with the pre-determined sets of signal characteristics; and generating output information based on the derived indication of position and orientation.

Variations, options and examples described in relation to the on-body sensor system outlined above may each be applied equally to the above method.

According to one set of embodiments, the above configuration method may further include performing an initial system training procedure in accordance with the training method defined above, in order to determine the pre-determined sets of signal characteristics for subsequent use in any of one or more iterations of the steps of the configuration method.

According to one set of embodiments, the configuration method may further comprise a re-calibration procedure for re-calibrating the dataset of pre-determined signal characteristics based on a known initial position of the receiver unit, the procedure for optionally performing in advance of the steps for deriving the indication of position and orientation outlined above. Optionally it may be performed after the initial training procedure mentioned above, and before the position determination.

The re-calibration procedure may comprise, for a known initial position of the receiver unit, controlling transmission of signals between the at least one transmitter unit and receiver unit, and deriving a set of signal characteristics associated with signals received at the receiver, comparing the derived set of signal characteristics with the pre-determined set of signal characteristics in the data set corresponding to said known initial position of the receiver unit; and correcting the pre-determined signal characteristics of the dataset based on any differences between the derived characteristics and the pre-determined characteristics.

Preferably, based on any derived differences, a correction factor may be derived, and this applied to each of the pre-determined signal sets of characteristics in the dataset, to thereby update the dataset.

These and other advantages will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1A:
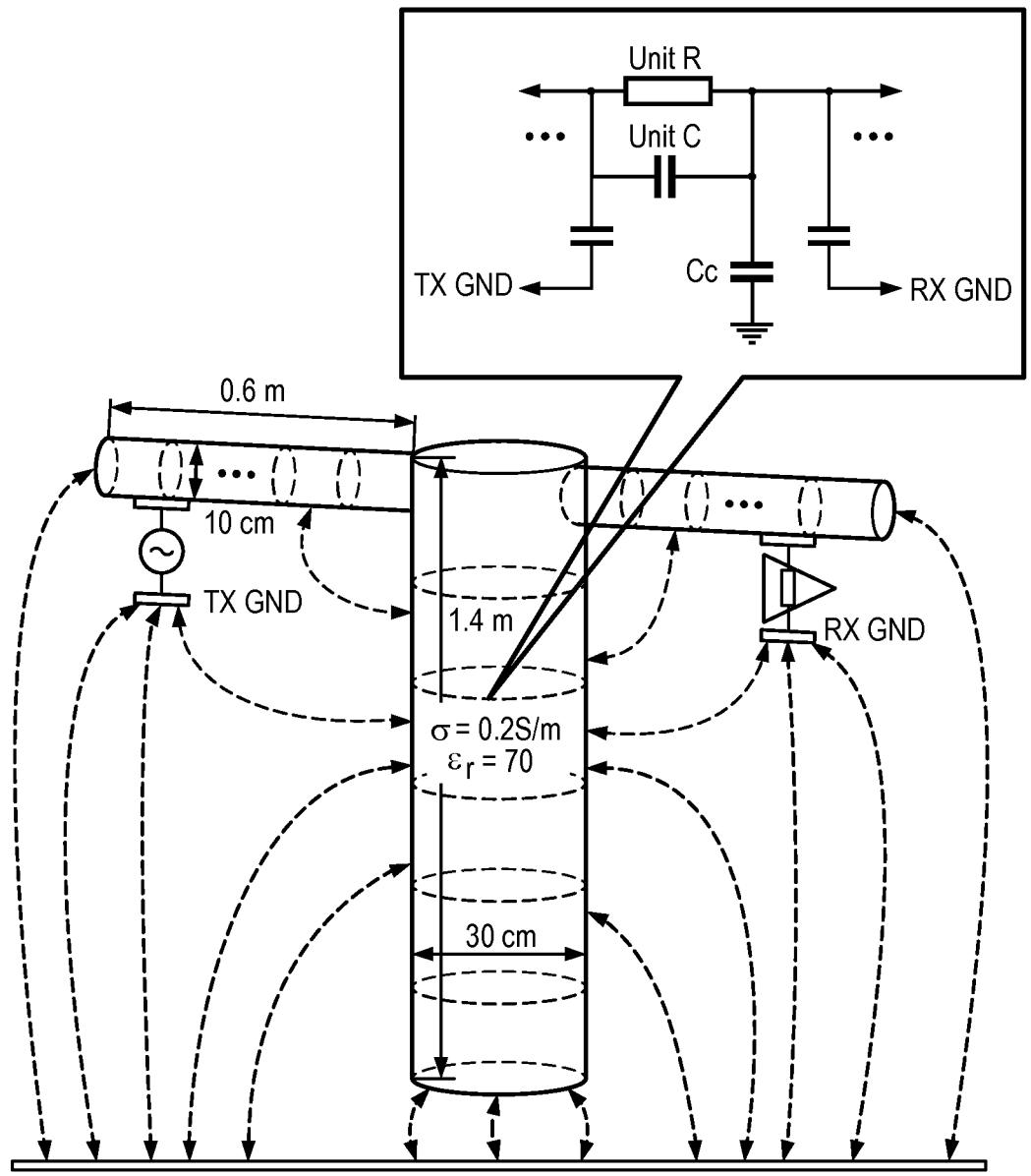
FIGS. 1(a) and 1(b) schematically depict a near field coupling model of the human body according to the prior art.
Figure 1B:
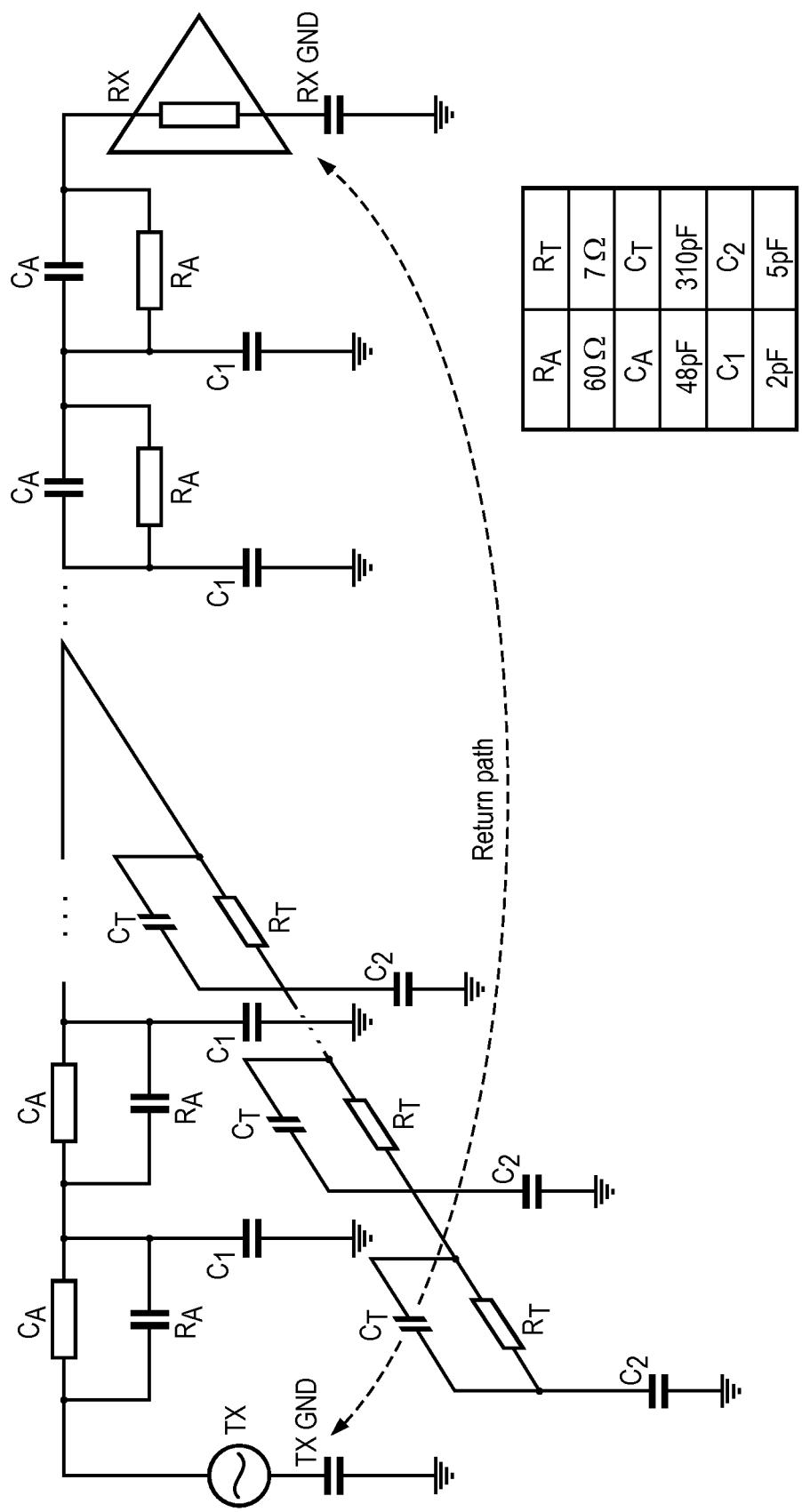
Figure 2:
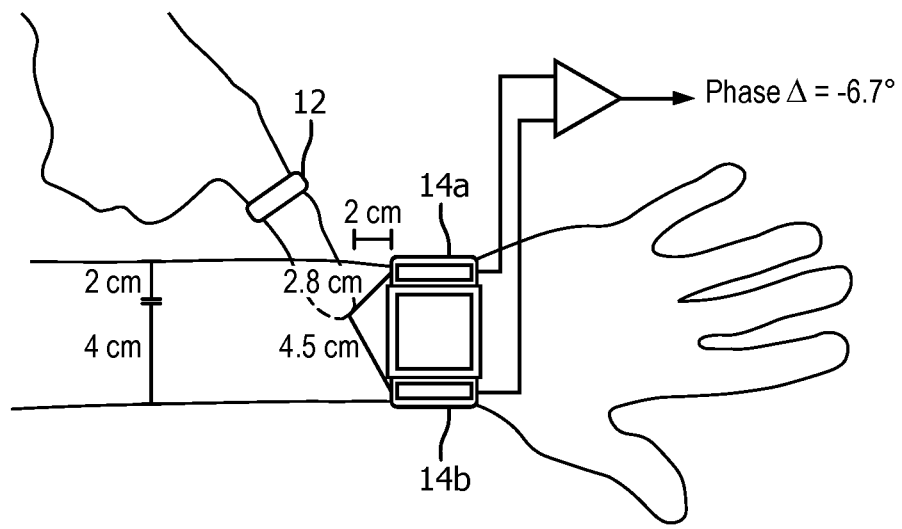
FIG. 2 schematically depicts a prior art technique for determining on-body position based on body-transmitted AC signals.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods described herein will become better understood from the following description, appended claims, and accompanying drawings. It should be understood that the Figures are merely schematic and are not drawn to scale. It should also be understood that the same reference numerals are used throughout the Figures to indicate the same or similar parts.

An on-body or handheld sensor system may be provided having means for determining a position of a skin interface unit based on transmission and receipt of electrical signals to the unit from a known transmitter location, transmitted via electrical channels of the body. By comparing sensed signal characteristics of the received signals with a plurality of sets of pre-determined signal characteristics, each set associated with one of a plurality of different reference positions and/or orientations of the receiver on the body, it may be possible to derive an indication of the position of the receiver unit on the body. Advantageously, this may then be used to provide guidance instructions for a user in moving the receiver unit closer to a defined target location on the body.

The embodiments described herein are aimed at allowing an on-body or handheld sensor unit, for instance for monitoring one or more physiological parameters, to continue to be used for an extended period by a patient at home after being discharged. A sensor patch of the system will often need to be replaced on a regular basis. When the patient positions the new patch, they may position it inaccurately. The system may determine an indication of position of the patch, and optionally may guide placement by a patient based on this.

The embodiments described herein may be based on deriving a body signal fingerprint for the receiver, composed of a set of plural signal characteristics associated with the received signal. This set of characteristics may uniquely characterizes or identifies the receiver position. By comparing this with multiple sets of pre-determined characteristics for known positions, the positon may be derived.

Figure 3:
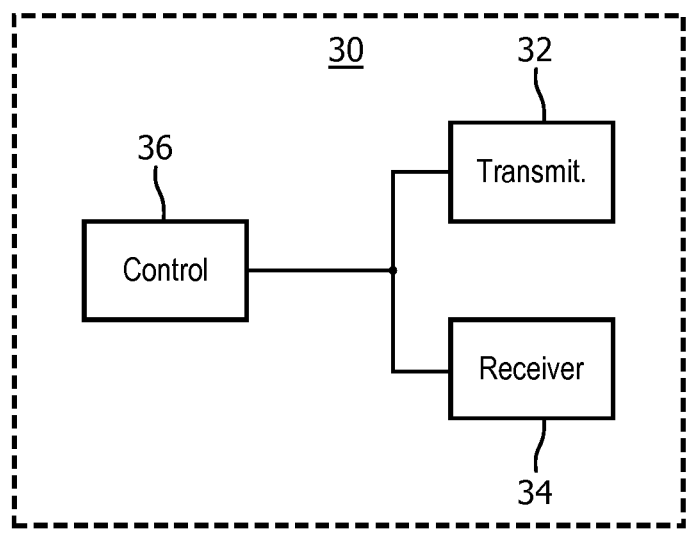
FIG. 3 shows in block diagram form an example system in accordance with one or more embodiments.

FIG. 3 schematically depicts in block diagram form an example on-body sensing system 30 in accordance with one or more embodiments.

The system may include two skin interface units 32, 34 for coupling electrical signals into and/or out of the body of a subject. The skin interface units may include a transmitter unit 32 for coupling signals into the body, and at least one receiver unit 34 for sensing the coupled signals. In use, the transmitter unit may be placed or mounted against a known region of the skin of the subject and the receiver unit may be placed or mounted against a different location of the body, remote (separated) from that of the transmitter. It is noted that although FIG. 3 shows the transmitter and receiver units as being adjacent to one another, this is schematic only. In use, with the system positioned in situ on the body of a subject, the transmitter and receiver units are preferably located remote from one another on the body.

The system further includes a controller 36, operatively coupled with the skin interface units 32, 34. The controller may be adapted to control transmission of signals between the at least one transmitter unit and receiver unit.

In FIG. 3, the controller 36 is shown as a separate dedicated control unit. However, as noted above, in other examples, the control function may be performed by one or more of the skin interface units 32, 34 themselves. Hence, in the latter case, the controller may be a distributed controller, or its control function may be distributed. Hence one or more of the skin interface units may comprise the controller in some examples, i.e. the control function may be distributed among the skin interface units of the system.

In some examples, each of the skin interface units may comprise a local control module for performing at least part of the control functionality of the overall system. For instance, each may control at least its own transmitting or receiving function. One of the units may be designated to perform the processing or determination steps (for determining an indication of position or generating guidance information for instance). There may be performed a configuration step in which the skin interface units communicate and designate one of the units as responsible for the determination steps.

In the following description, reference to the controller 36 may be understood as referring either to a dedicated control unit or to one or more of the skin interface units of the system performing the relevant control function.

As will be explained in greater detail below, the circuitry for generating signals and for processing received signals may be distributed in different ways between the components of the system. In some examples, this circuitry may be all comprised by a central controller 36. In other examples, the transmitter unit 32 may comprise local circuitry for generating electrical signals. In other examples, the signals may be generated externally, for instance by a central controller.

The controller 36 may be further adapted to derive a set of signal characteristics associated with each signal received at the receiver, the characteristics being dependent on position and/or orientation of the receiver unit. The signal characteristics may be directly measured from properties of the received signals, or may alternatively be derived or computed from the properties of the signals. They may include by way of example one or more of: signal transmission time ('time of flight' between signal transmission and receipt), signal attenuation between transmitter and receiver (path loss), and phase angle difference between at least two electrodes comprised by the receiver unit 34.

The set of derived signal characteristics may define a body finger print (BFP) corresponding to the current placed location of the receiver unit 34.

The system 30 may be a physiological parameter monitoring system. In particular, one or both of the skin interface units 32, 34 may be for sensing one or more physiological signals (such as electrocardiogram (ECG) or electromyography (EMG) signals for example). Accurate positioning of the skin interface unit(s) (in particular the receiver unit) may be in this case important in order that monitoring of these physiological parameters is accurate.

To assist in this, the controller 36 may be configured to derive an indication of position and orientation of the receiver unit.

The controller 36 may have access to a dataset comprising a plurality of pre-determined sets of signal characteristics, each set associated with one of a plurality of different reference positions and/or orientations of the receiver on the body. The indication of position and orientation of the receiver 34 may be derived based on comparing the derived set of signal characteristics for the received signals with the pre-determined sets of signal characteristics in the data set. The dataset may be stored locally, e.g. in a memory comprised by the system, or stored remotely e.g. in the cloud or a remote computer with which the controller is communicable.

Output information may be generated by the controller 36 based on the derived indication of position and orientation.

Although only two skin interface units are shown in the example of FIG. 3, in further examples, a greater number of interface units may be provided. In particular examples there may be provided a plurality of transmitter units 32. In further examples, a plurality of receiver units may additionally or alternatively be provided.

Where a plurality of transmitter units 32 are provided, the controller may be adapted to control the multiple signal transmitter units sequentially, configuring each in turn to transmit signals as transmitter. Signals may be sensed at the receiver 34 for each transmitter, and for each one a separate set of signal characteristics corresponding to the received signals from that transmitter may be derived or measured. The full collection of signal characteristics from all transmitters may be grouped to form a single overall set of signal characteristics (a single body finger print (BFP)) for the given receiver location.

The controller 36 may be configured to identify a total number of transmitter units connected to the system 30.

The skin interface units 32, 34 may take different forms.

The transmitter unit 32 may be an on-body unit for mounting against a pre-determined region of the skin of the subject, or an off-body unit for temporary placement against a pre-determined region of the skin of the subject.

For example, the transmitter unit 32 may be a wearable unit configured for mounting to a particular part of the body. In advantageous examples, the transmitter unit may be in the form of a wrist mountable device. This carries the advantage that the position of the transmitter unit in this case may be stable and reliably known. However, this effect may also be achieved with other body-mounted devices that may be fixedly secured to a part of the body, e.g. a chest strap, ankle band or car hook by way of example.

The transmitter unit 32 may be in the form of a smart watch device in examples. The smart watch device may comprise the controller 36 according to examples.

The transmitter unit 32 may alternatively take the form of an off-body unit such as a weight scale.

The receiver unit 34 may be in the form of a sensor patch or pad for mounting against the skin of the subject. The sensor patch may comprise a flexible electrode or one or more flexible electrode pairs for sensing electrical signals from the skin or body. The patch may have an adhesive layer for coupling the patch to the skin. Receiver unit 34 may also be included in a handheld device. For example, a handheld ultrasound device may include capacitive micromachined ultrasonic tranducer (cMUT) arrays for image acquisition.

The receiver unit 34 may be for use also in monitoring one or more physiological parameters as part of a physiological parameter monitoring function of the system 30. The physiological parameters may be vital signs for instance.

The output information generated by the controller 36 may be guidance information for guiding a user in positioning the receiver unit 34 at a defined target location. The output information may simply comprise a representation or indication of the derived position and/or orientation indication for example. Output information may be communicated from the controller to a user output means, for example a sensory output means, for communication to a user. The sensory output means may for instance be a display and/or a speaker.

Where the output information is guidance information, the controller 36 may be configured to compare the derived indication of position and orientation with a defined target position and orientation, and to generate guidance information based on said comparison, for guiding the user in positioning the receiver unit at the target position and orientation.

The target position may be pre-programmed. For example, it may be one of a pre-determined set of positions known to provide accurate monitoring of physiological parameters of interest using the receiver unit 34. The target position may be at least partially user-defined, for example via a user input means. For example, the target position may be input by a clinician before a patient leaves hospital, or one of a set of pre-defined target positions may be selected. The target position may be one of the reference positions to which the sets of predetermined signal characteristics in the dataset correspond.

The provision of output information (based on the determined receiver position) in the form of guidance information may assist a user, e.g. a patient, to correctly position a sensor element (e.g. a sensor patch, handheld device) in a target position. This may be necessary since, as noted above, sensor patches typically need replacing every few days once a patient returns home.

One example procedure for guiding correct placement of the devices described herein (e.g., patch, handheld device, etc.) will now be described by way of illustration only. Although a patch is used through the examples, various other devices, such as handheld devices as described herein, may be positioned using similar components and/or methods.

According to this example, the procedure of guiding placement of the patch may be performed in two stages. In a first stage, correct position placement may be implemented. In a second stage, correct orientation placement may be implemented.

According to the first stage, the user performing the placement of the receiver unit 34 may place the unit at an initial position P. With the receiver at position P, transmission of signals from the transmitter unit 32 to the receiver unit may be controlled, and a set of signal characteristics for the signals derived, to thereby derive a body finger print (BFP) for position P.

This BFP may be compared with the various BFPs comprised in the dataset of pre-determined sets of signal characteristics. Based upon this comparison, a proximity of P to each of the reference positions to which each of the pre-determined sets of signal characteristics (predetermined BFPs) correspond may be determined. Various algorithms for implementing such a proximity determination may be employed. One example for instance may be found in the paper Belay, A. et al (2017, May). Indoor localization at 5 GHz using Dynamic machine learning approach (DMLA). In Applied System Innovation (ICASI), 2017 International Conference on (pp. 1763-1766). IEEE.

A distance metric may then be computed which gives an indication of a distance between the current receiver location and the defined target location. For example the defined target location may be one of the positions represented within the dataset of pre-determined signal characteristics.

It may then be determined whether the receiver 34 lies within a defined acceptable proximity threshold of the target position. If the target location is outside of the set bounds, the controller 36 may generate output information for guiding a user to reposition the receiver unit 34 in a new position which is closer to the target location. The guidance information may minimize the remaining distance metric to the target location. The controller may output an indication of a distance that the receiver must be moved to arrive at the target location, e.g. an indication of the distance metric itself. The controller also may determine an indication of a displacement direction between the receiver location and the target location, and includes this information in the output guidance information.

Once the user has moved the receiver unit 34 to a position at which the distance metric may be within the defined proximity threshold, output information may be generated for indicating to the user that the receiver should be fixed at the corresponding body location.

Following correct position placement, in the second stage, guidance information may be generated for guiding the user in correctly orienting the receiver device. With the receiver unit at the correct position on the body, the user may begin orienting, i.e. rotating relative to the skin, the receiver unit 34. For each orientation, the controller may determine a new set of signal characteristics. These may be compared with a corresponding set of signal characteristics stored in the pre-determined dataset for a defined target orientation. Based on this comparison, an error metric may be computed, providing an indication of an angular disparity between the current orientation and the target orientation.

If the derived error metric is outside of a defined tolerance threshold, the controller may generate output information for guiding a user to reorient the receiver unit 34 in a new orientation which is closer to the target orientation. The guidance information may be such that the remaining error metric is minimized. Once the user orients the mobile wearable device correctly such that the error metric is within set bounds (i.e. within the tolerance threshold), output information may be generated to indicate to the user to stop orienting the receiver unit 34.

Correct position and orientation of the receiver unit may be thereby achieved.

As discussed, the procedure carried out by the controller may involve determining one or more signal characteristics associated with signals receiver at the receiver unit 34. This will now be explained in greater detail.

The one or more derived signal characteristics may include by way of example phase angle, signal transmission time, and signal attenuation between transmission and receipt. Transmission time may mean signal time of flight: propagation duration between initial transmission and receipt. Signal attenuation means signal path loss: change in signal strength between initial transmission and receipt. Other signal characteristics may additionally or alternatively be derived.

Deriving the signal time of flight (transmission time) may be achieved simply by recording the time of transmission of the signal and the time of receipt of the signal and calculating the difference. For performing this, the at least one transmitter unit 32 and the at least one receiver unit may each comprise an internal clock and the clocks may be synchronized. A central controller 36 may track the time of transmission of the signal and receipt of the same signal at the receiver unit. Directly sequential transmission and receipt events may be assumed to be associated with the same signal.

Deriving the path loss (signal attenuation) may be achieved simply by recording the signal strength at transmission (or generating the signal for transmission at a known strength) measuring the strength of the same signal on receipt, and then computing the change. The strength of the signal may refer for example to signal amplitude, e.g. in volts, for example peak-to-peak amplitude. The receiver unit 34 and the transmitter unit 32 may each comprise signal processing means permitting measurement of the signal strength, e.g. signal amplitude. In this case, each of the units may comprise a clock, and the clocks may synchronized, allowing the transmission and receipt of a given signal to be matched to one another. In particular, directly sequential transmission and receipt events may be assumed to be associated with the same signal. However, alternatively a central controller may comprise signal processing means for measuring the signal strength of signals received at the receiver unit, e.g. amplitude, and may be configured to calculate a signal attenuation between transmission and receipt.

The at least one receiver unit 34 may include two or more pairs of electrodes. In this case, advantageously, one or more differential signal characteristics may be derived, corresponding to a difference in the value of a given signal characteristic between two pairs of electrodes of the receiver unit 34.

For example, the differential signal characteristic may be one or more of: phase angle difference, signal transmission time (time of flight) difference and signal attenuation (path loss) difference. In each case the difference may be between the value as measured at each of two electrode pairs of a receiver unit 34. The value of the differential signal characteristic for the receiver unit may be determined by the controller 36 for example, or may be determined locally by the receiver unit 34. Optionally, a differential value may be derived for one or more signal characteristics in respect of each and every combination of electrode pairs comprised by the receiver unit (where there are more than two).

A differential signal characteristic provides a particularly precise characterization of positioning, and in particular orientation, since the difference in the measured values at two spatially separated electrode pairs varies consistently depending on orientation state.

Figure 4:
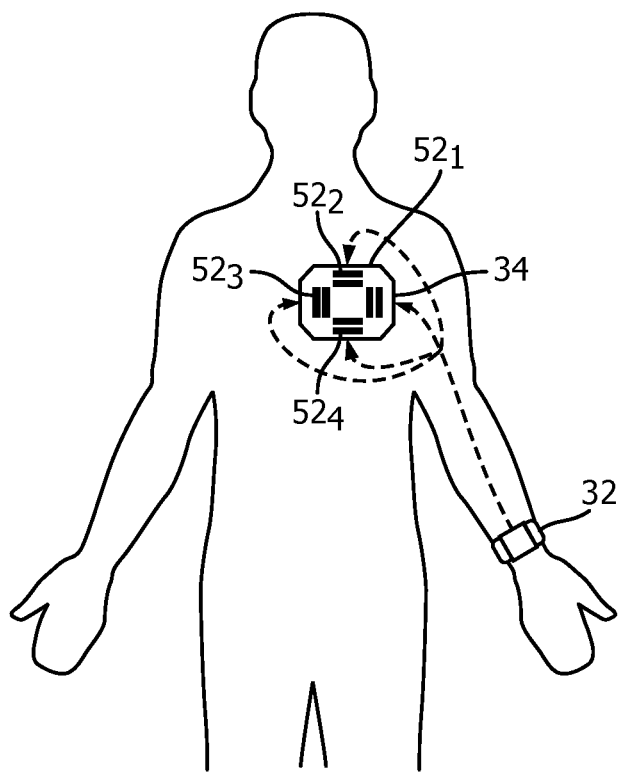
FIG. 4 schematically illustrates an example system according to an embodiment.

To illustrate, FIG. 4 shows an example receiver unit 34 comprising four pairs of electrodes $52_1$, $52_2$, $52_3$, $52_4$. The receiver unit may be shown positioned in situ on the body, along with a transmitter unit 32 in the form of a wrist-mounted device. All possible phase angle differences between the signal that may be received at the at least two electrode pairs of the receiver unit may be described as follows:

$$\emptyset_{ij} = \emptyset_i - \emptyset_j,$$

which indicates the phase angle difference $\emptyset$ between the signal received at electrode pairs $52_i$ and $52_j$ respectively. Accordingly, all phase angle differences $\emptyset_j$ between an electrode pair $52_i$ and itself, where i=1, 2, 3, 4, is zero. The phase angle difference $\emptyset_{ij}$ between electrode pairs $52_i$ and $52_j$ respectively is the same but the opposite sign to the phase angle difference $\emptyset_{ji}$ between electrode pairs $52j$ and $52_i$, i.e. $\emptyset_{ij} = -\emptyset_{ji}$, where i=1, 2, 3, 4 and j=1, 2, 3, 4 and when i≠j.

For example, $\emptyset_{12} = \emptyset_1 - \emptyset_2$ indicates the phase angle difference between the signal received at the electrode pairs $52_1$ and $52_2$, and so on. Thus, where the receiver unit 34 is orientated as shown in FIG. 4, the phase angle difference $\emptyset_{13}$ between the signal received at electrode pairs $52_1$ and $52_3$ respectively will be negative and the phase angle difference $\emptyset_{31}$ between the signal received at electrode pairs $52_i$ and $52_1$ respectively will be positive indicating that electrode pair $52_1$ is closer to the transmitter unit 32 than the electrode pair $52_3$.

The phase angle difference $\emptyset_{24}$ between the signal received at electrode pairs $52_2$ and $52_4$ and the phase angle difference $\emptyset_{42}$ between the signal received at electrode pairs $52_4$ and $52_2$ will be zero (or almost zero) due to an equal (or almost equal) distance between the electrode pairs 1021 and 1024 and the transmitter unit 32. The phase angle difference $\emptyset_{12}$ between the signal received at electrode pairs $52_1$ and $52_2$ and phase angle difference $\emptyset_{14}$ between the signal received at electrode pairs $52_1$ and $52_4$ will be small but negative and phase angle difference $\emptyset_{32}$ between the signal received at electrode pairs $52_3$ and $52_2$ and the phase angle difference $\emptyset_{34}$ between the signal received at electrode pairs $52_i$ and $52_4$ will be small but positive. These phase angle differences may characterize in a precise way the orientation of the receiver unit 34 with respect to the transmitter unit 32.

A body fingerprint which includes such a differential signal characteristic is advantageous for enabling orientation of the receiver unit to be derived, based on a dataset which also includes this characteristics associated with known corresponding orientations.

As discussed, another possible differential signal characteristics which may additionally or alternatively be derived may be a time of flight (ToF) of the signal received at one of the at least two electrode pairs $52_1$, $52_2$, $52_3$, $52_4$ of the receiver unit 34 relative to a time of flight of the signal received at at least one other of the at least two electrode pairs $52_1$, $52_2$, $52_3$, $52_4$ of the receiver unit 34. The relative time of flight of the signals may be also indicative of an orientation of the receiver unit with respect to the transmitter unit 32. More specifically, the longer the time of flight of the signal received at an electrode pair $52_1$, $52_2$, $52_3$, $52_4$, the further away the electrode pair is from the transmitter unit. Similarly, the shorter the time of flight of the signal received at an electrode pair, the closer the electrode pair is to the transmitter unit.

For example, where the receiver unit 34 is orientated as shown in FIG. 4, the time of flight $t_1$ from the transmitter unit 32 to the electrode pair $52_1$ may be lowest compared to the time of flight $t_2$, $t_3$ and $t_4$ from the transmitter unit 32 to the electrode pairs $52_2$, $52_3$ and $52_4$ respectively. The time of flight t; from the transmitter unit 32 to the electrode pair $52_3$ has the highest value, while the time of flight $t_2$ and $t_4$ from the transmitter unit 32 to the electrode pairs $52_2$ and $52_4$ respectively will be equal (or almost equal) and less than the time of flight $t_3$ from the transmitter unit 32 to the electrode pair $52_3$ but greater than the time of flight $t_1$ from the transmitter unit 32 to the electrode pair $52_1$.

Thus, where the receiver unit 34 is orientated as shown in FIG. 4, the relative time of flight of the signals can be described as follows:

$$t_1 \leq t_2, t_4 \leq t_3.$$

This can provide information in particular on the orientation of the receiver unit 34 with respect to the transmitter unit 32. Where the property is a time of flight (ToF), the receiver unit 34 may be time synchronized with the transmitter unit 32 prior to the transmission of the signal from the transmitter unit 32 (for example, in the manner described earlier). The receiver unit 34 may generate a reference signal using an internal synchronized clock of the receiver unit 34. The reference signal can provide a reference to the signal transmitted from the transmitter unit 32. A central controller 36 may keep track of the times of transmission and receipt.

As discussed, a signal characteristics which may additionally or alternatively be derived may be amplitude of the signal received at one of the at least two electrode pairs $52_1$, $52_2$, $52_3$, $52_4$ relative to an amplitude of the signal received at at least one other of the at least two electrode pairs $52_1$, $52_2$, $52_3$, $52_4$. In these examples, the relative amplitude of the signals may be indicative in particular of the orientation of the receiver unit 34 with respect to the transmitter unit 32.

Due to the impedance of the body, the signal transmitted from the transmitter unit 32 may undergo attenuation as it travels through the body. Thus, the amplitude of the signal transmitted from the transmitter unit 32 may decrease as it travels through the body. Attenuation of the signal occurs. The longer the signal travels through the body, the more the signal may be attenuated (or the more the amplitude of the signal decreases). Thus, the lower the amplitude of the signal received at an electrode pair $52_1$, $52_2$, $52_3$, $52_4$ of the receiver unit 34, the further away the electrode pair $52_1$, $52_2$, $52_3$, $52_4$ is from the transmitter unit 32. Similarly, the higher the amplitude of the signal received at an electrode pair of the receiver unit 34, the closer the electrode pair is to the transmitter unit 32.

For example, where the receiver unit 34 is orientated as shown in FIG. 4, the amplitude of the signal received at the electrode pair 52$_3$ may be lowest compared to the amplitude of the signal received at the other electrode pairs 52$_1$, 52$_2$ and 52$_4$. Similarly, the amplitude of the signal received at the electrode pair 52$_1$ may be highest compared to the amplitude of the signal received at the other electrode pairs 52$_2$, 52$_3$ and 52$_4$. The amplitude of the signal received at the electrode pairs 52$_2$ and 52$_4$ is equal (or almost equal) and less than the amplitude of the signal received at the electrode pair 52$_1$ but greater than the amplitude of the signal received at the electrode pair 52$_3$.

In some embodiments, the signal attenuation G may be derived as follows:

$$G=20\ \log_{10}(V_{receive}/V_{send}),$$

where $V_{receive}$ is the amplitude of the signal received at the at least two electrode pairs 52$_1$, 52$_2$, 52$_3$, 52$_4$ of the receiver unit 34 and $V_{send}$ is the amplitude of the signal transmitted from the transmitter unit 32.

The greater the signal attenuation of the signal received at an electrode pair 52$_1$, 52$_2$, 52$_3$, 52$_4$ of the receiver unit 34, the further away the electrode pair is from the transmitter unit 32. Similarly, the lesser the attenuation of the signal received at an electrode pair of the receiver unit 34, the closer the electrode pair 52$_1$, 52$_2$, 52$_3$, 52$_4$ is to the transmitter unit 32. Thus, where the receiver unit 34 is orientated as shown in FIG. 4, the attenuation of the signal received at the electrode pair 52$_1$ is greater than the attenuation of the signal received at the electrode pair 52$_2$ and the attenuation of the signal received at the electrode pair 52$_4$ may be less than the attenuation of the signal received at the electrode pair 52$_3$.

The above explanations represents an example of signal characteristics which may be derived and do not limit the invention. Advantageously both differential signal characteristics (differences in signal characteristics values between two pairs of electrodes of the receiver unit) may be calculated in addition to absolute values of the same signal characteristics. The latter may be particularly useful for inclusion in the body fingerprint for characterizing and thus deriving position of a receiver unit. The former may be especially useful for characterizing orientation.

As mentioned above, handling of signal generation and processing functions may be distributed between components of the system 30 in different ways. In one set of examples, signal generation and processing of received signals may be performed centrally by the (central) controller 36, wherein the first and second skin interface units are simply for electrically coupling generated and received signals into and back out from the body. They may each simply comprise one or more electrodes for facilitating this for instance.

Signal generation and the processing of received signals may be distributed between the skin interface units. For example, the first skin interface unit 32 (the transmitter unit 32) may comprise circuitry for generating the signals for applying to the body, and the second skin interface unit (the receiver unit 34) may comprise circuitry for processing the sensed signals.

Also, both the nominal transmitter 32 and receiver 34 units may each be selectably configurable either as signal generator (i.e. transmitter) or as signal sensor (i.e. receiver). Hence the functionality of the two may be interchangeable.

Each may comprise circuitry both for generating signals for coupling into the body and for processing signals coupled back out of the body. Each skin interface unit may hence be switchable between the two modes or functionalities, to thereby increase flexibility of the system. Such a skin interface unit may be termed a multi-function interface unit.

Figure 5:
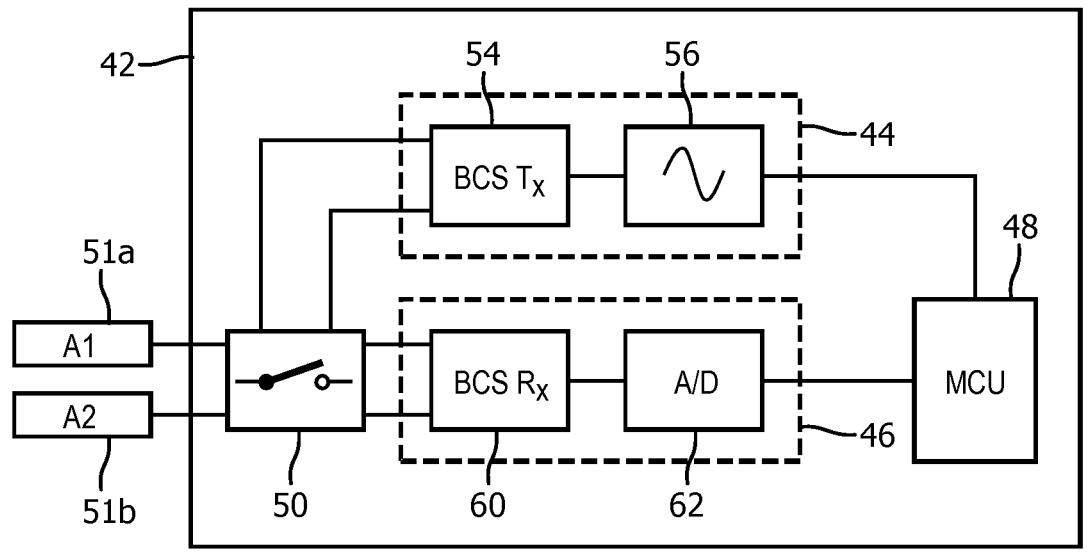
FIG. 5 shows in block diagram form an example signal transceiver as may be used in example systems according to one or more embodiments.

FIG. 5 shows, in block diagram form, circuitry which may be comprised by such a multi-function skin interface unit, to permit implementation of both signal generation (transmission) and processing of received signals.

The circuitry together may form a transceiver unit 42 for controlling generation and transmission of signals through the body via the given skin interface unit, and also for receiving of signals at a remote location via a second skin interface unit. This transceiver unit may be referred to as an RF unit.

The transceiver unit 42 includes in this example one set of components for controlling signal generation and transmission (transmitter circuit part 44) and a second set of components for controlling receiving of signals (receiver circuit part 46). Both parts are operatively connected to a microcontroller unit (MCU) which controls the transmitter 44 and receiver 46 parts. Both the transmitter and receiver parts may be connected with a switch 50 which interfaces with two skin contacting electrodes 51a, 51b, dubbed electrode A1 and A2. More than one pair of electrodes may be included in further examples. The switch 50 may be for switching the given interface unit 32, 34 between signal transmission mode (which connects the electrodes to the transmitter circuit part 44) and signal receiving mode (which connects the electrodes to the receiver circuit part 46).

The signal transmission part 44 includes a signal generator 56 adapted to generate electrical signals for coupling into the skin by the electrodes 51. The signal generator advantageously generates alternating signals at radio frequencies. Preferably, signals may be generated in a frequency range 10 MHz to 150 MHz as in this frequency range the human body behaves as a waveguide for signal transmission.

The transmitter part 44 may further include a voltage booster and driver 54 adapted to receive the generated raw signals, amplify (i.e. boost) them and drive application of the signals, via the switch and electrodes 51, to the body.

The signal receiver part 46 may include an analog front end element 60 for receiving in analogue form, via the switch 50, the raw signals sensed by the electrodes 51. The front end element may communicate the received signals to an analogue-to-digital converter 62 which processes the signals and outputs them in digital form to the microcontroller unit 48.

In other examples, each of the skin interface units 32, 34 may be configured to perform only one of signal generation or signal sensing. In this case, each may comprise only one of the transmitter 44 or receiver 46 circuit parts shown in FIG. 5, and the switch may be omitted. For instance, the nominal transmitter unit 32 may comprise only the transmitter circuit part 44, and the nominal receiver unit 34 may comprise only the receiver circuit part 46.

In further examples, both the transmitter 44 and receiver 46 circuit parts of the transceiver unit 42 shown in FIG. 5 may be comprised by the central controller 36, with the controller 36 configured to electrically communicate signals to and from the skin interface units 32, 34.

The illustrated transceiver unit 42 shown in FIG. 5 represents a circuitry which may be used to generate and process signals in accordance with embodiments. Other suitable circuitry implementations, capable of achieving similar functionality, will be apparent to the skilled person.

To illustrate these concepts, an embodiment will now be described in detail, by way of example only.

Figure 6:
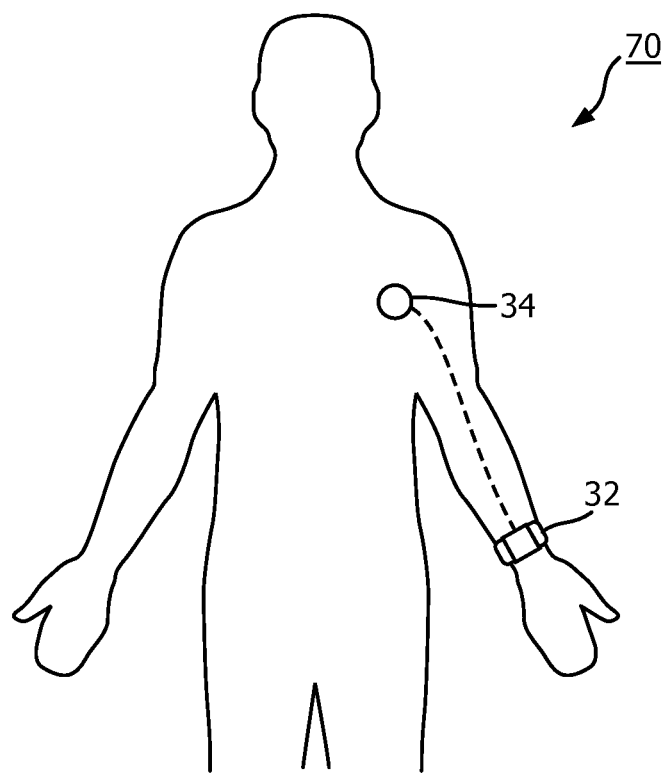
FIG. 6 schematically depicts an example on-body sensor system according to an embodiment.

A layout of the system 30 according to this embodiment is illustrated schematically in FIG. 6. Although a patch is used through the examples, various other devices, such as handheld devices as described herein, may be positioned using similar components and/or methods. The system is illustrated in situ with components attached to or mounted on the body of a subject 70. The system may comprise a transmitter unit 32 in the form of a smart watch or other related device. The transmitter unit may constitute a first skin interface unit, for coupling generated signals into the body. The system may comprise a receiver unit in the form of a sensor patch 34. The sensor patch may constitute a second skin interface unit, for sensing the signals coupled into the body by the smart watch device. Although a single transmitter unit is provided in this example, multiple transmitter units may alternatively be provided.

Although a smart watch may be used, a different wearable device could be used in accordance with other examples of this embodiment. Also, an off-body device could be used such as a smart weight scale or a handheld device. This provides the same advantage that the location of the device on the body is reliably known, as it is configured for application to a particular location on the skin of the subject (i.e. the feet in this case).

The wearable device 32 and sensor patch 34 may each comprise a plurality of electrodes for directly interacting with the skin. Preferably, the wearable device may include one or more pairs of electrodes, configured as transmitter electrodes. Preferably the sensor patch may include at least one pair of electrodes, configured as receiver electrodes.

The wearable device 32 and sensor patch 34 may each comprise a transceiver circuit 42 as illustrated in FIG. 5 and described above. For the sensor patch, the circuit may be configured for receiving (body channel signal (BCS) receiver circuit 46 is active), while for the wearable device transmitter, the circuit may be configured for transmitting (body channel signal (BCS) transmitter circuit 44 is active). Alternatively, the patch may comprise only the receiver circuit part 46, and the wearable device may comprise only the transmitter circuit part 44.

The system may further comprise a dedicated controller (not shown). Alternatively, the control function may be performed by one or more of the skin interface units 32, 34. For example, the controller may be comprised by the wearable device 32, or the wearable device may form or constitute the controller, i.e. may perform the function of the controller. Reference to a controller may be taken as referring to either option.

Communication between the patch 34 and wearable device 32 may be facilitated via any suitable communication medium or channel, either wired or wireless. For reasons of comfort and flexibility, wireless communication may be preferred. Both the wearable device 32 and patch 34 may in this case comprise wireless communication modules to facilitate this. These may comprise standard communication technologies such as Bluetooth, Wi-Fi, ultra-wide band (UWB) or body-coupled communication for instance.

In use, the wearable device 32 may be mounted to a known location on the body as shown in FIG. 6, i.e. the wrist in this case.

The controller 36 may be configured to determine an indication of position and orientation of the sensor patch 34. To implement this, a set of signal characteristics corresponding to signals transmitted between the wearable device 32 and the patch 34 may be determined.

For example, each electrode pair comprised by the transmitter unit 32 may be controlled to couple an electrical signal into the skin of the body (a body channel signal (BCS)) for transmission via electrical body channels of the body. The electrode pairs may be controlled to couple signals one at a time in a sequential manner. For each of these transmitted BCS signals, each electrode pair comprised by the patch 34 (the receiver unit) may receive the signal.

For each received signal, a set of multiple signal characteristics may be derived. These may be based on directly measured properties of the signals or may be derived or computed from the measured signal properties.

Example procedure for deriving various signal characteristics at the receiver unit have been described in detail above.

In the case that the receiver patch 34 has only one pair of electrodes, it may be possible to measure signal characteristics including signal attenuation (path loss (PL)) and signal transmission time (time of flight (ToF)) of the received signal. If the receiver patch has more than one pair of electrodes, it may be possible to measure differential signals such as phase angle difference, ToF difference, PL difference between two receiver electrode pairs. Optionally, multiple sets of measurements can be performed for different signal transmission frequencies. As discussed above, where the system 30 comprises multiple transmitter units, each transmitter may be controlled to transmit signals through the body in turn and separate sets of signal characteristics derived for the signals received from each. When two or more transmitter units are present, optionally, one may be configured to operate as a Master transmitter to coordinate the process of sequentially configuring each transmitter unit to transmit signals. A separate central controller 36 may perform this function.

There are thus multiple available degrees of freedom for building up the body finger print. Multiple sets of signal characteristics can be derived for each of multiple possible electrode pairs on each receiver and transmitter, and for multiple transmitters. This allows a very comprehensive body finger print to be generated allowing detailed characterization of a particular body location, and thus more precise receiver localization.

As an example, for a given position and orientation of the receiver unit 34 on the body, there may be M receiving electrodes comprised by the receiver unit 34, N transmitting electrodes comprised by the transmitter unit 32, P transmitter units in total, and a set of Q different signal characteristics which can be derived in each case. In this case, it may be possible to obtain a set of M*Q signal characteristic measurements for each electrode pair of each respective transmitter unit. Hence, for a single transmitter unit, it may be possible to obtain N*M*Q signal characteristic measurements. For the full set of transmitter units, it may be possible to obtain a set of P*N*M*Q signal characteristic measurements.

Furthermore, it also possible to add to this (P*N*($^M C_2$)*Q) combinations of pairwise differential signal s characteristic measurements, i.e. differences in derived signal characteristics between different electrode pairs of the receiver unit 34. Hence, the total number of obtainable signal characteristic measurements in this example is (P*N*M*Q)+(P*N*($^M C_2$)*Q) measurements.

Further still, each of the measurements may be repeated for F different signal frequencies. In this case, it may be possible to obtain for each receiver unit position a set of (F*P*N*Q)(M+*($^M C_2$)) different signal characteristics.

As noted above, the complete set of signal characteristics for a given body position of a receiver unit 34 may be termed the body finger print of the receiver unit with respect to the transmitter unit(s) 32 for a given position and orientation on the body.

A given body finger print can be expressed as $BPF_{i,j}$ where i indexes the particular body channel characteristics of the complete set (i.e. i={1,2,3, . . . . (F*P*N*Q)(M+*($^M C_2$))}) and j={1,2,3, . . . . J} for J different possible positions and or orientations (a.k.a locations) of the receiver unit 34 on the body.

It may be to be noted that the above example is one of many possible ways by which to build a comprehensive body finger print (BFP). In further examples, other or additional signal characteristics may be derived for each signal, and other options and variations will be apparent to the skilled person.

It may be noted that certain measured or computed signal characteristics may vary with position of the receiver unit 34 while other parameters vary with orientation. Hence, it is possible to independently derive indications of position and orientation, by considering in each case only the appropriate subset of signal characteristics, and comparing these with only the corresponding appropriate subset of the pre-determined signal characteristics.

Embodiments are based on comparing a sensed set of signal characteristics with a dataset of pre-determined signal characteristics, each set associated with one of a plurality of different reference positions and/or orientations of the receiver on the body. In this way, an indication of position and orientation for the receiver unit 34 may be derived.

To facilitate this, there may be a system training method for initially establishing the dataset of multiple pre-determined sets of signal characteristics. This may be performed once as an initial set-up procedure, and the derived data set then used for each subsequent iteration of a position determination procedure by the system. It may be performed for instance by a nurse or other hospital personnel during initial application of the patch to a patient in a hospital or other care facility. It also may be performed by a medical professional or technician during imaging applications as described with reference to handheld imaging devices. Although a patch is used through the examples, various other devices, such as handheld devices as described herein, may be positioned using similar components and/or methods.

To perform the system training procedure, the nurse or other personnel first mounts one or more transmitter units 32 on or against the patient's body. For instance, the transmitter units may be wearable devices such as wrist-mountable devices, or may be one or more off-body devices such as a smart weight scale. The transmitter units are configured to perform as transmitters (e.g. in the case that the unit comprises a generic transceiver unit 42 such as that of FIG. 5 above). A receiver unit 34, such as a sensor patch, may be also prepared for mounting to the body, and this may be configured as the receiver.

The receiver unit 34 may be placed at a first particular position and orientation on the body. A particular control mode may be triggered on the controller 36 in order to activate the training procedure, e.g. a particular app may be launched. Transmission of signals between the transmitter and receiver units may be controlled by the controller 36, and a first set of signal characteristics (i.e. a first body finger print (BFP)) corresponding to the received signals for the first location may be derived. This may be stored, either locally in a memory or in the controller or transmitter unit 34 (e.g. wearable device) or stored remotely, for instance in the cloud.

Then nurse or other personnel then sequentially places the receiver unit 34 at multiple other locations (position and orientation) on the body and for each position and orientation, a corresponding set of signal characteristics (a corresponding BFP) may be derived and stored. The thus formed complete dataset of signal characteristics for the multiple different receiver locations may be compiled and stored, either locally or remotely. It may be stored at the controller and/or the receiver unit. It may additionally or alternatively be stored in the cloud.

The nurse or other personnel then designates one of the trial positions and orientations as a target position and orientation at which the patient should be guided by the system to place the patch or device when they come to replace and/or re-mount it. This designation may be stored, again locally and/or remotely.

Figure 7:
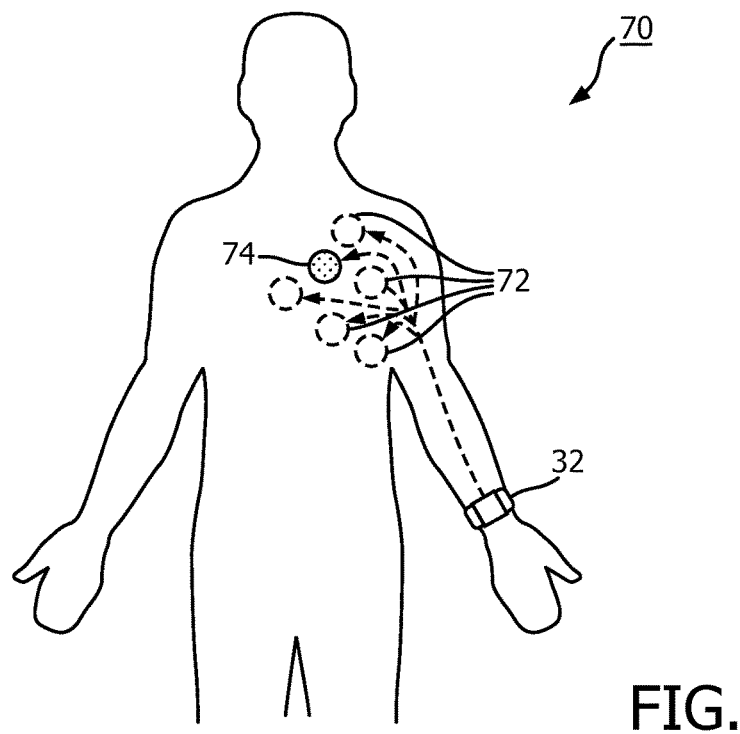
FIGS. 7 and 8 schematically illustrate system-training procedures for establishing a dataset of pre-determined signal characteristics for different reference positions of a receiver unit of the system.
Figure 8:
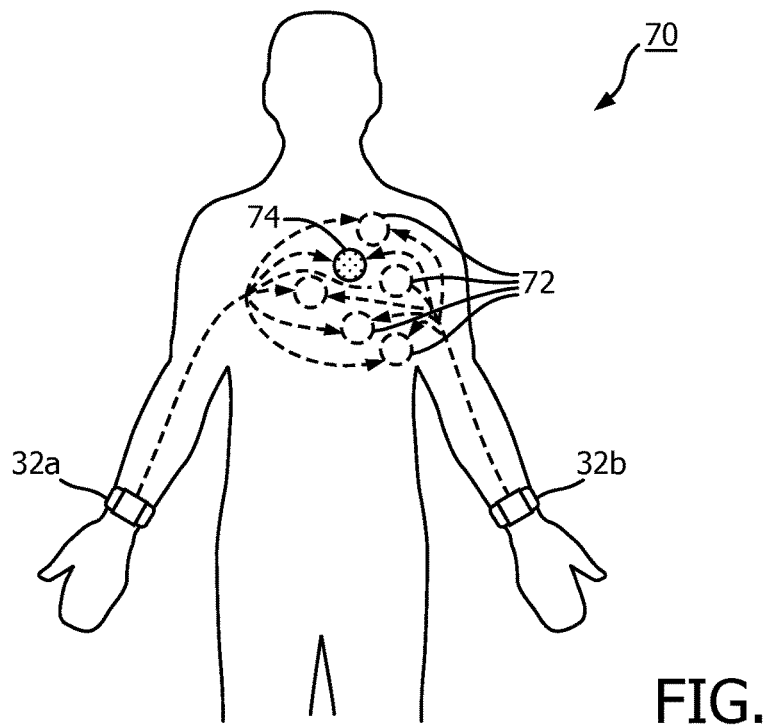

The procedure is illustrated schematically in relation to two example on-body sensor systems in FIGS. 7 and 8. FIG. 7 shows the example sensor system of FIG. 6, comprising a single sensor patch 34 as receiver unit and a single wrist-worn transmitter unit 32. The multiple dotted circles indicate the various reference positions and orientations 72 to which the patch may be sequentially moved throughout training method. The filled circle illustrates the single assigned target position and orientation 74 at which the user will be guided to place the patch by the system when replacing the patch at home. Again, although a patch is used through the examples, various other devices, such as handheld devices as described herein, may be positioned using similar components and/or methods.

FIG. 8 illustrates the process in relation to a second example on-body sensor system comprising two transmitter units 32a, 32b, each in the form of a wrist-worn device. Again, the dotted circles indicate the various reference positions and orientations 72 to which the patch may be sequentially moved and the filled circle illustrates the assigned target position and orientation 74 for later localization of the patch. In this case however, for each position and orientation 72, each of the transmitter units 32a, 32b may be activated in turn to generate and transmit signals and sets of signal characteristics derived for the signals of each transmitter. The signal characteristics for both transmitter units are combined to form a single comprehensive set of signal characteristics for each position and orientation (i.e. to form a single body finger print (BFP) for each location).

An aspect may include a method of configuring placement of skin interface units of an on-body sensing system. This involves determining an indication of a placed position of one skin interface unit (the receiver unit), and (in preferable embodiments) providing guidance information to a user for guiding the user in repositioning the unit closer toward a defined target position. As discussed above, such a method finds particularly beneficial application where the system may be for at-home monitoring of one or more physiological parameters over an extended period after the patient has been discharged from hospital, and where the receiver unit may be for use in measuring those parameters. The receiver unit e.g. a sensor patch, often needs to be frequently replaced which necessitates the patient repositioning it on their body after its replacement. Accurate positioning is important to ensure reliable and accurate parameter monitoring, but can be difficult without medical training.

Figure 9:
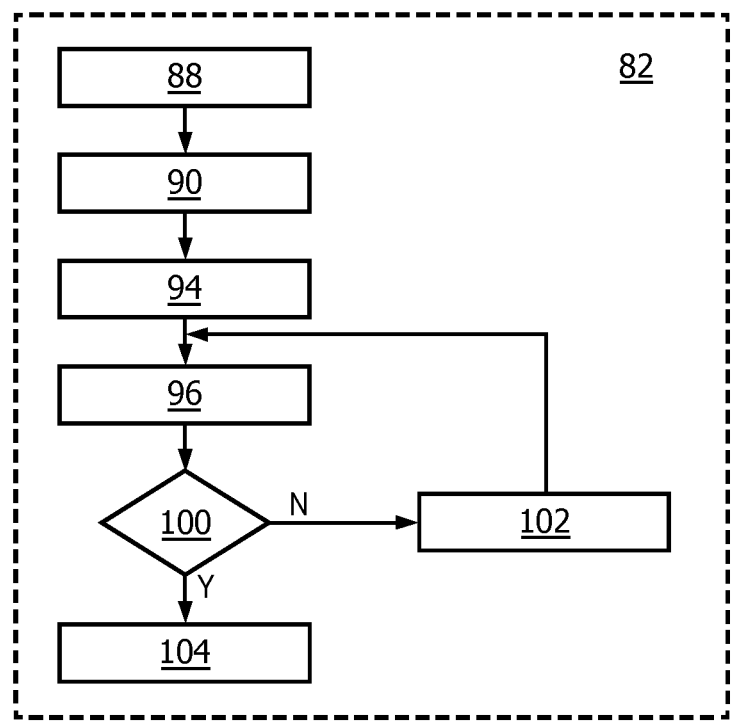
FIG. 9 shows in block diagram form an example method for configuring position of a receiver unit of an on-body sensor system according to an embodiment.
Figure 10:
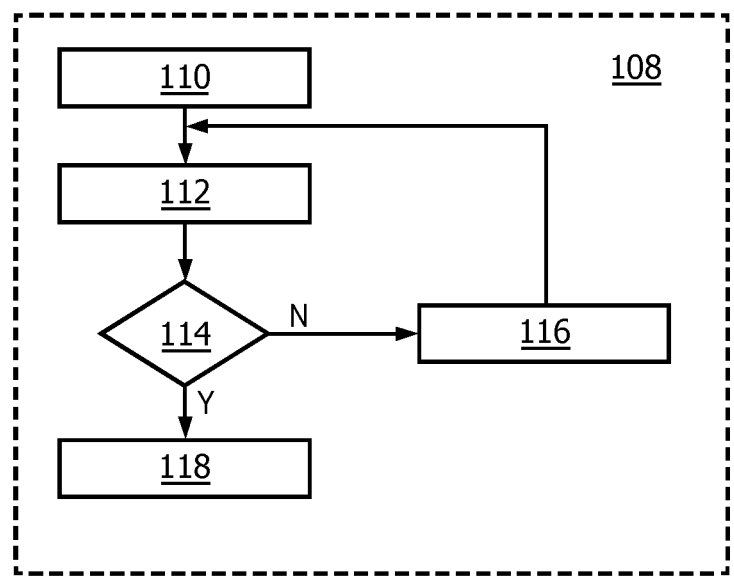
FIG. 10 shows in block diagram form an example method for configuring orientation of a receiver unit of an on-body sensor system according to an embodiment.

By way of illustration, one example method for configuring placement of a receiver unit of a sensor system will now outlined, with reference to FIG. 9 and FIG. 10. The described example is for illustration only and is not intended to be limiting.

The placement method may be divided into two sequential stages: a first 82 for placement of the receiver unit at a target position (shown in block diagram form in FIG. 9) and a second 108 for orienting the receiver in a target orientation (shown in block diagram form in FIG. 10).

Referring to FIG. 9, in a first step 88, the user may remove the current receiver unit (e.g. sensor patch) for replacement by a new unit. Optionally, the dataset of predetermined signal characteristics for different reference positons may need to be transferred onto the new patch. This data also may be stored in a central controller 36.

A target position and orientation for placement of the new device on the body may be acquired 90. This may be pre-assigned by a nurse, in which case, this step comprises retrieving the stored assigned target position and orientation. The user also may set or select the target position and orientation. This may be chosen from the set of reference positions and orientations to which the pre-determined signal characteristics of the dataset correspond. The user may then trigger the device placement procedure on the system, e.g. by triggering a particular control mode on a controller 36, or launching a particular app, and places 94 the new device (e.g., patch or handheld device) in an initial first position. The transmitter unit 32 may be controlled to transmit signals and the signal characteristics are derived for the signals received at the receiver patch, to thereby form a body finger print (BFP) for the initial position. This may be compared with the pre-determined set of signal characteristics (the pre-determined BFP) in the dataset for the assigned target position.

An indication of current position may be derived based on computing 96 a distance metric between the measured BFP and the pre-determined BFP in the dataset for the target position. The paper Belay, A. et al (2017, May). Indoor localization at 5 GHz using Dynamic machine learning approach (DMLA). In Applied System Innovation (ICASI), 2017. International Conference on (pp. 1763-1766). IEEE. describes various algorithms which may be used to compute this.

Based on the distance metric, the current position of the device with respect to the target position may be determined. It may be determined 100 whether the distance metric between the current position and the target position is small enough that the device is within a defined acceptable proximity threshold. The proximity threshold may be configurable, e.g. by user input, or may be pre-defined. It may be defined based on the required accuracy or precision of the device placement.

If the device is not within the allowable proximity threshold ("NO"), guidance information may be generated and output 102 to the user for guiding the user in repositioning the device closer to the target positon. The guidance preferably includes indication of a direction and distance that the device should be moved in order to minimize the distance metric. The distance metric calculation 96 and checking 100 steps may then be repeated. If and when the device is found to be within the proximity threshold of the target position, output information may be generated 104 for indicating to the user that the device is in the correct position and should be mounted, affixed or held in place at the current position. Following correct positioning, the second stage of the placement procedure comprises placement of the device in the correct orientation. FIG. 10 shows in block diagram form the steps of this stage.

Once the correct position is reached, the user orients the device 110, if desired, in a first initial orientation 110. A set of signal characteristics (BFP) may be derived as described above for the initial orientation. An error metric may be computed 112 by comparing the current orientation BFP with the BFP in the pre-determined dataset corresponding to the target position.

It may be determined 114 whether the error metric is small enough to place the device within a defined angular proximity threshold of the target orientation. If the orientation is outside the defined bounds ("NO"), guidance information may be generated and output 116 to the user for guiding the user in reorienting the device closer to the target orientation. The guidance information preferably includes an indication of an angular distance and direction in which the device should be moved to minimize the error metric. The error metric calculation 112 and checking 114 steps may be repeated.

If and when the device is found to be within the proximity threshold of the target orientation, output information may be generated 118 for indicating to the user that the device is in the correct position and correct orientation and should be mounted, affixed, or held in place at the current position and orientation.

The skin interface unit placement method may be complete.

As discussed above, embodiments may make use of a dataset of predetermined sets of signal characteristics (BFPs) for different reference positions and orientations.

Figure 11:
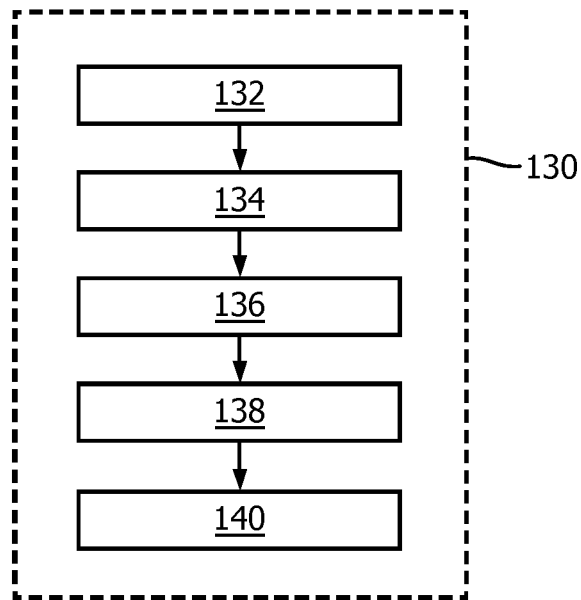
FIG. 11 shows in block diagram form an example system training method for establishing a dataset of pre-determined signal characteristics for different reference positions of a receiver unit of the system.

One example system training method 130 for establishing the dataset of pre-determined signal characteristics for different reference positions will now be outlined in more detail with reference to FIG. 11. This may be for performing in advance of placement of the receiver unit, e.g. in accordance with the method of FIGS. 9 and 10. Hence this procedure may be performed once in advance of step 88 of the method of FIG. 9. The steps of the method of FIGS. 9 and 10 may be repeated as many times as required in subsequent iterations without repeating the system training method of FIG. 11.

With reference to FIG. 11, in a first step 132 of the example training method 130, a nurse or clinician may indicate to the controller 36 that system training is being carried out by triggering a particular control mode on the controller or for instance launching an app. The nurse or other user may then place 134 the receiver unit (e.g. a patch for this example) on the patient's body in multiple different positions and orientations, and for each one a set of signal characteristics (a BFP) may be derived 136 in accordance with the approach described in previous examples. This may be repeated for N locations to derive N sets of signal characteristics (BFPs) which may be denoted $BFP_j$ with $j=\{1, 2, 3 \ldots . N\}$.

The full set of BFPs may be may be stored 138 as a dataset in a local memory and/or remotely, e.g. in the cloud. They may be stored locally at the transmitter unit and/or a central controller 36.

The user may attach 140 the patch at one of the reference positions and preferably stores on the system, locally or remotely, an indication of which position the patch is fixed at. Preferably the nurse also stores a designated target location at which the patient will be guided in placing the patch during the subsequent placement procedure.

The signal characteristics making up a body fingerprint (BFP) corresponding to a particular receiver position and orientation may change over time due to changing skin properties such as moisture levels. Hence the pre-determined sets of signal characteristics in the dataset may become inaccurate over time. This can lead to inaccurate position and orientation determination if the pre-determined signal characteristics are not updated or corrected. Thus, in accordance with one or more advantageous embodiments, the system configuration method may further include a calibration step in which the pre-determined sets of signal characteristics are corrected.

The calibration method may assume a known initial positon of the receiver unit 34, e.g. based on a known position in which the receiver was placed by a nurse or clinician (e.g. stored by them during an initial training or calibration procedure), or based on an earlier determined position. The method may include controlling transmission of electrical signals between the transmitter unit 32 and receiver unit 34, and deriving a set of signal characteristics associated with the received signals. These form a body fingerprint corresponding to the current location of the receiver. This derived set of signal characteristics may be compared with the pre-determined set of characteristics corresponding to the same, current known location of the patch. The pre-determined signal characteristics may be corrected based on any differences between the newly calculated characteristics and the previous characteristics.

Preferably, based on any derived differences, a correction factor may be derived, and this applied to each of the sets of pre-determined signal characteristics in the dataset, to thereby update the dataset.

Although a patch is used through the examples, various other devices, such as handheld devices as described herein, may be positioned using similar components and/or methods.

Figure 12:
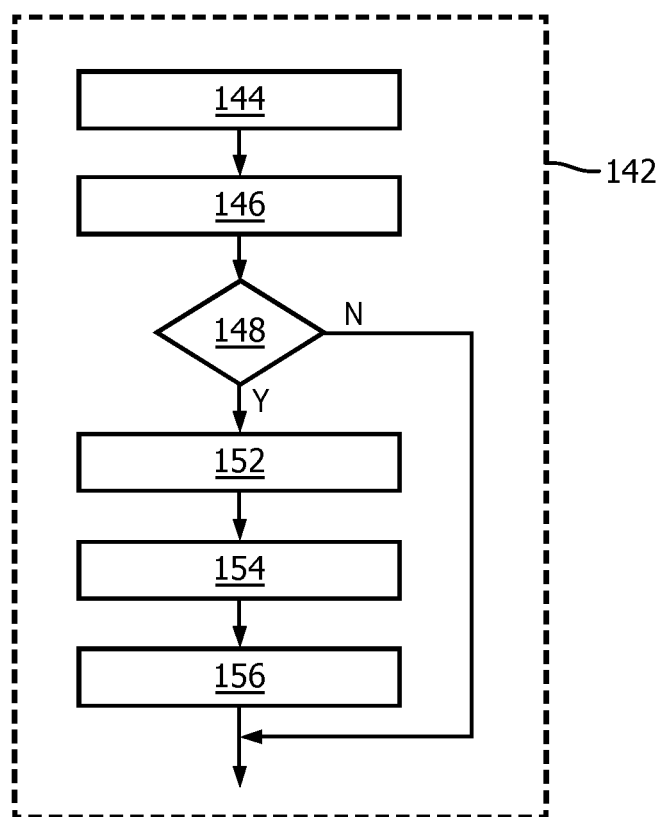
FIG. 12 shows in block diagram form an example re-calibration method for correcting a pre-determined dataset signal characteristics.

FIG. 12 shows in block diagram form one example calibration method which will now be outlined in greater detail. The calibration method (if needed) may be for performing subsequent to the initial training method for establishing the dataset of pre-determined sets of signal characteristics (e.g. in accordance with the method of FIG. 11). However, the calibration method (if needed) may be performed in advance of the receiver unit placement method of FIGS. 9 and 10. It may be for performing between these two procedures. Again, although a patch is used through the examples, various other devices, such as handheld devices as described herein, may be positioned using similar components and/or methods.

With reference to FIG. 12, in a first step 144 of the calibration procedure 142, the patient or other user may trigger the patch re-calibration procedure on the central controller 36. The transmitter unit 32 may be controlled to transmit signals via the body and a set of signal characteristics for the signals received at the receiver patch 34 in its initial position and orientation are derived 146.

It may be determined 148 whether the derived signal characteristics for the current (initial, known) position differ from the pre-determined signal characteristics for the same position stored in the dataset. If not ("NO"), then no re-calibration may be required. If there are differences, a correction factor may be determined 152 between the measured signal characteristics (or BFP) for the current position and the pre-stored signal characteristics for that same position. The correction factor should be suitable to map or transform the pre-stored set of characteristics to the newly derived characteristics. The pre-determined characteristics for the known position may be updated according to the newly derived ones.

The correction factor may be applied 154 to the each of pre-determined sets of signal characteristics (BFPs) stored in the dataset for the various different reference positions and orientations in order thereby to correct the dataset to compensate for the changed skin conditions.

The updated dataset of pre-determined sets of signal characteristics (BFPs) may be stored 156 in place of the previous dataset, locally (e.g. at the controller and/or patch and/or transmitter unit) and/or remotely, e.g. in the cloud or a remote computer with which the controller or system may be communicable.

Output information may be generated 156 for indicating to the user that the re-calibration procedure may be complete.

Once re-calibration is complete, the user may remove the patch from their body in order to replace it.

The various methods and procedures outlined above and illustrated in FIGS. 9-12 may be combined in a sequential order according to certain examples, to thereby provide a fully comprehensive on-body sensor system configuration method.

Accordingly, in summary, according to the most comprehensive embodiments, the on-body sensor system configuration method can be understood as a four-step procedure:

Step 1: System training procedure to establish the dataset of pre-determined signal characteristics for different reference positions (e.g. in accordance with the method of FIG. 11).

Step 2: Re-calibration procedure to correct the established dataset for any skin property changes (e.g. in accordance with the method of FIG. 12).

Step 3: Receiver unit position placement procedure (e.g. in accordance with the method of FIG. 9).

Step 4: Receiver unit orientation placement procedure (e.g. in accordance with the method of FIG. 10).

While the above embodiments of the invention are described in the form of a patch it is clear that they can be advantageously applied to handheld devices which are contacted with the body, as described throughout this disclosure. An example of such a class of device is a hand held imaging sensor and in particular a hand held ultrasound device, which may comprise a cMUT array for image acquisition.

As discussed above, embodiments may make use of a dedicated controller 36. The controller can be implemented in numerous ways, with software and/or hardware, to perform the various functions required. A processor may be one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICS), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An on-body sensor system, comprising:
at least two skin interfaces for at least one of: coupling electrical signals into the body of a subject or coupling electrical signals out of the body of the subject, the at least two skin interfaces comprising: (i) at least one transmitter for placement against a known region of the skin of the subject for coupling signals into the body, and (ii) at least one receiver for placement at a remote location, for sensing the coupled signals; and
a controller operably coupled with the skin interfaces for controlling transmission of signals between the at least one transmitter and the at least one receiver, and deriving a set of multiple signal characteristics associated with each signal received at the at least one receiver, the multiple signal characteristics comprising at least one signal characteristic being dependent on a position of the at least one receiver and at least one signal characteristic being dependent on an orientation of the at least one receiver;
wherein the controller has access to a dataset comprising a plurality of pre-determined sets of signal characteristics, each set associated with one of a plurality of different reference positions of the at least one receiver on the body and a plurality of different orientations of the at least one receiver on the body; and
wherein the controller derives an indication of the position and the orientation of the at least one receiver based on comparing the derived set of signal characteristics for the received signals with the pre-determined sets of signal characteristics, and generating output information based on the derived indication of the position and the orientation of the at least one receiver.

2. The on-body sensor system as claimed in claim 1, wherein the controller compares the derived indication of the position and the orientation of the at least one receiver with a defined target position and orientation, and generates guidance information based on said comparison, for guiding a user in positioning the at least one receiver at the target position and orientation.

3. The on-body sensor system as claimed in claim 2, wherein the controller derives an indication of distance between the derived position and the target position based on said comparison, the output information being based on this derived distance.

4. The on-body sensor system as claimed in claim 2, wherein the controller determines a displacement direction between the derived indication of position and the target position, and wherein the output information comprises an indication of this direction.

5. The on-body sensor system as claimed in claim 3, wherein the controller generates guidance information based on said derived distance and direction to the target position for moving the at least one receiver to minimize the distance between the at least one receiver and the target position.

6. The on-body sensor system as claimed in claim 1, wherein the at least one receiver comprises at least two pairs of skin-coupling electrodes.

7. The on-body sensor system as claimed in claim 6, wherein the derived set of signal characteristics includes a separate subset of signal characteristics derived for each of the electrodes.

8. The on-body sensor system as claimed in claim 1, wherein the controller identifies a total number of transmitters, and, in the case that that there is more than one, controls transmission of signals by each transmitter in turn, and derives a separate set of signal characteristics associated with the signals received from each transmitter.

9. The on-body sensor system as claimed in claim 1, wherein the at least one receiver is in the form of an on-body sensor patch.

10. The on-body sensor system as claimed in claim 1, wherein
the at least one transmitter is in the form of a wearable device for mounting to a particular part of the body, or
the at least one transmitter is in the form of an off-body device for temporary placement against the skin of a particular part of the body.

11. The on-body sensor system as claimed in claim 1, wherein the on-body sensor system is for monitoring one or more physiological parameters of a subject, and wherein the at least one receiver is for use in sensing the one or more physiological parameters.

12. The on-body sensor system as claimed in claim 1, wherein the signal characteristics include one or more of: signal transmission time, signal attenuation between transmitter and receiver, or phase angle difference between at least two electrodes comprised by the at least one receiver.

13. A method of training an on-body sensing system for configuring placement of at least two skin interfaces of a system,
wherein the system comprises the at least two skin interfaces for at least one of coupling electrical signals into the body of a subject or coupling electrical signals out of the body of the subject, wherein each of the at least two skin interfaces comprise: (i) at least one transmitter for placement against a known region of the skin of the subject for coupling signals into the body, and (ii) at least one receiver for placement at a remote location, for sensing the coupled signals,
the method comprising:
sequentially placing the at least one receiver in each of a plurality of different reference positions and reference orientations on the body, and for each position or orientation, controlling transmission of signals between the at least one transmitter and the at least one receiver, and deriving a set of multiple signal characteristics associated with the signals received at the at least one receiver for that position and orientation; and
storing the plural sets of signal characteristics for the plurality of different reference positions and orientations, to thereby derive a dataset of pre-determined signal characteristics, the dataset for use in subsequently deriving indications of the position and orientation of the receiver, based on comparing sensed signal characteristics with the stored pre-determined characteristics.

14. A method of configuring placement of at least two skin interfaces of an on-body sensing system, wherein the system comprises the at least two skin interface for at least one of coupling electrical signals into the body of a subject or coupling electrical signals out of the body of the subject, wherein the at least two skin interfaces each comprise: (i) at least one transmitter for placement against a known region of the skin of the subject for coupling signals into the body, and (ii) at least one receiver or placement at a remote location, for sensing the coupled signals, the method comprising:
controlling transmission of signals between the at least one transmitter and receiver, to derive a set of multiple signal characteristics associated with each signal received at the at least one receiver, the multiple signal characteristics comprising at least one characteristic being dependent on a position of the at least one receiver and at least one characteristic being dependent on an orientation of the at least one receiver;
accessing a dataset comprising a plurality of pre-determined sets of signal characteristics, each set associated with one of a plurality of different reference positions and orientations of the at least one receiver on the body;
deriving an indication of position and orientation of the at least one receiver based on comparing the derived set of signal characteristics for the received signals with the pre-determined sets of signal characteristics; and
generating output information based on the derived indication of position and orientation.

15. The method as claimed in claim 14, the method further comprising:
sequentially placing the at least one receiver in each of a plurality of different reference positions and reference orientations on the body, and for each position or orientation, controlling transmission of signals between the at least one transmitter and the at least one receiver, and deriving a set of signal characteristics associated with the signals received at the at least one receiver for that position and orientation; and
storing the plural sets of signal characteristics for the plurality of different reference positions, to thereby derive a dataset of pre-determined signal characteristics, the dataset for use in subsequently deriving indications of the position and orientation of the at least one receiver based on comparing sensed signal characteristics with the stored pre-determined characteristics.

16. The on-body sensor system as claimed in claim 3, wherein the controller determines whether the derived distance is within a defined acceptable proximity threshold of the target distance, and generates guidance information for positioning the at least one receiver closer to the target position only in the case that the distance is outside of the acceptable threshold.

17. The on-body sensor as claimed in claim 10, wherein the particular part of the body is a wrist.

* * * * *